United States Patent
Tamura et al.

(10) Patent No.: US 8,530,446 B2
(45) Date of Patent: Sep. 10, 2013

(54) ORAL COMPOSITION CONTAINING DIFRUCTOSE ANHYDRIDE

(75) Inventors: Akiko Tamura, Yokohama (JP); Norihiro Shigematsu, Yokohama (JP); Hiroshi Hara, Sapporo (JP)

(73) Assignee: Fancl Corporation, Yokohama-shi, Kanagawa (JP)

( * ) Notice: Subject to any disclaimer, the term of this patent is extended or adjusted under 35 U.S.C. 154(b) by 1592 days.

(21) Appl. No.: 11/719,239

(22) PCT Filed: Oct. 25, 2005

(86) PCT No.: PCT/JP2005/019597
§ 371 (c)(1),
(2), (4) Date: Jun. 26, 2007

(87) PCT Pub. No.: WO2006/054429
PCT Pub. Date: May 26, 2006

(65) Prior Publication Data
US 2009/0069269 A1    Mar. 12, 2009

(30) Foreign Application Priority Data
Nov. 17, 2004 (JP) ................................ 2004-333663

(51) Int. Cl.
*A01N 43/04* (2006.01)
*A61K 31/715* (2006.01)
*A61K 31/70* (2006.01)

(52) U.S. Cl.
USPC ............................... 514/53; 514/25; 514/874

(58) Field of Classification Search
USPC ............................................. 514/53, 25, 874
See application file for complete search history.

(56) References Cited

U.S. PATENT DOCUMENTS

| 5,925,190 A | 7/1999 | Richards |
| 2006/0069062 A1 * | 3/2006 | Shiomi et al. ................... 514/53 |

FOREIGN PATENT DOCUMENTS

| EP | 1214893 A1 | 6/2002 |
| EP | 1504761 A1 * | 2/2005 |
| JP | 63-269962 | 11/1988 |
| JP | 07-506822 | 7/1995 |
| JP | 11-043438 | 2/1999 |
| JP | 2000-204042 | 7/2000 |
| JP | 2003-321371 | 11/2003 |
| JP | 2004-161619 | 10/2004 |
| JP | 2005-225838 | 8/2005 |
| WO | WO 99/07392 | 2/1999 |
| WO | WO 99/44621 | 9/1999 |
| WO | WO 03/090759 A1 | 11/2003 |
| WO | WO 2004/078989 A1 | 9/2004 |

OTHER PUBLICATIONS

Kearns, G.L., Abdel-Rahman, S.M., Alander, S.W., Blowey, D.G., Leeder, J.S., Kauffman, R.E. (2003) Developmental Pharmacology—Drug Disposition, Action, and Therapy in Infants and Children. New England Journal of Medicine, vol. 349, p. 1147-1167.*
Picherit, C., Coxam, V., Bennetau-Pelissero, C., Kati-Coulibaly, S., Davicco, M.-J., Lebecque, P., Barlet, J.-P. (2000) Daidzein is More Efficient than Genistein in Preventing Ovariectomy-Induced Bone Loss in Rats. The Journal of Nutrition, vol. 130, p. 1675-1681.*
Ohta, A., Uehara, M., Sakai, K., Takasaki, M., Adlercreutz, H., Morohashi, T., Ishimi, Y. (2002) A Combination of Dietary Fructooligosaccharides and isoflavone Conjugates Increases Femoral Bone Mineral Density and Equol Production in Ovariectomized Mice. Journal of Nutrition, vol. 132, p. 2048-2054.*
Setchell, K.D.R., Brown, N.M., Zimmer-Nechemias, L., Brashear, W.T., Wolfe, B.E., Kirschner, A.S., Heubi, J.E. (2002) Evidence for lack of absorption of soy isoflavone glycosides in humans, supporting the crucial role of intestinal metabolism for bioavailability. American Journal of Clinical Nutrition, vol. 76, p. 447-453.*
Remington's The Science and Practice of Pharmacy, 19th Edition, editor Alfonso R. Gennaro, published by Mack Publishing Company (1995) p. 1650-1654.*
Suzuki, et al., "Various non-digestible saccharides increase intracellular calcium ion concentration in rat small-intestinal enterocyes," British Journal of Nutrition, 2004, vol. 92, pp. 751-755.
Chang, et al.,"Metabolism of Daidzein and Genistein by Intestinal Bacteria," Journal of Natural Products, 1995, vol. 58, No. 12, pp. 1892-1896.
Mariko Uehara, et al., "Fructooligosaccharide wa Daizu Isoflavon no Taisha o Shushoku suru—Mouth oyobi Rat deno Kento-," The Japanese Society of Nutrition and Food Science Sokai Koen Yoshishu, vol. 55, 2001, p. 132.
Mariko Uehara, et al., "Isoflavon Taisha ni Taisuru Fructooligosaccharide Sesshu no Eikyo—Kecchu Isoflavon oyobi Taisha Sanbutsu no Keijitsu Hendo-," The Japanese Society of Nutrition and Food Science Sokai Koen Yoshishu, vol. 56, 2002, p. 138.

* cited by examiner

*Primary Examiner* — Scarlett Goon
(74) *Attorney, Agent, or Firm* — Knobbe, Martens, Olson & Bear LLP

(57) ABSTRACT

An oral composition for increasing equol production by inner-intestinal bacteria, wherein such composition contains difructose anhydride as an active ingredient to activate the equol production function of inner-intestinal bacteria.

4 Claims, No Drawings

ORAL COMPOSITION CONTAINING DIFRUCTOSE ANHYDRIDE

This application is the U.S. National Phase under 35 U.S.C. §371 of International Application PCT/JP2005/019597, filed Oct. 25, 2005, which claims priority to Japanese Patent Application No. 2004-333663, filed Nov. 17, 2004. The International Application was published under PCT Article 21(2) in a language other than English.

BACKGROUND OF THE INVENTION

1. Technical Field

The present invention relates to an oral composition for increasing equol production by inner-intestinal bacteria.

2. Description of the Related Art

Compared to daidzein and genistein, which are representative isoflavones, equol provides better antioxidative activity and estrogen activity and is therefore expected to offer greater health benefits than the above substances. Equol is a metabolite produced when daidzein is metabolized in the intestines by inner-intestinal bacteria. Accordingly, activating the equol production function of inner-intestinal bacteria is likely to increase the amount of equol that can be utilized in our body.

On the other hand, difructose anhydride (hereinafter referred to as "DFA") is known to promote growth of bifidus bacillus (Patent Literature 1: Japanese Examined Patent Laid-open No. Hei 3-5788), increase calcium absorption (Patent Literature 2: Japanese Patent Laid-open No. Hei 11-43438) and provide diuretic effect (Patent Literature 3: Japanese Patent Laid-open No. 2003-321371). However, its ability to increase equol production has not heretofore been known.

Patent Literature 1: Japanese Examined Patent Laid-open No. Hei 3-5788
Patent Literature 2: Japanese Patent Laid-open No. Hei 11-43438
Patent Literature 3: Japanese Patent Laid-open No. 2003-321371

SUMMARY OF THE INVENTION

Problems to be Solved by the Invention

As mentioned above, increasing the equol production function of inner-intestinal bacteria is expected to realize health benefits. To increase the amount of equol that can be utilized in our body, the equol production function of inner-intestinal bacteria must be activated.

Means for Solving the Problems

After diligently examining ways to activate the equol production function of inner-intestinal bacteria, the inventors found that ingestion of difructose anhydride (hereinafter referred to as "DFA") would increase the blood equol level. In other words, the present invention relates to an oral composition for increasing equol production by inner-intestinal bacteria, characterized by containing DFA as an active ingredient.

To be specific, key constitutions of the present invention are listed below:

(1) An oral composition for increasing equol production by inner-intestinal bacteria, characterized by containing difructose anhydride as an active ingredient.
(2) An oral composition for increasing equol production by inner-intestinal bacteria, characterized by containing difructose anhydride and daidzein and/or derivative thereof.
(3) A drug, food or beverage containing an oral composition for increasing equol production by inner-intestinal bacteria according to (1) or (2).
(4) A drug or feed for pet animals containing an oral composition for increasing equol production by inner-intestinal bacteria according to (1) or (2).

Effects of the Invention

An oral composition containing DFA as proposed by the present invention increases the equol production function of inner-intestinal bacteria and thereby increases the blood equol level.

BEST MODE FOR CARRYING OUT THE INVENTION

DFA as mentioned in the present invention is a known substance. Specifically, it is an anhydro cyclic disaccharide constituted by two fructoses bonding at two positions each. DFA has been known to exist in caramel, etc., but industrially it can be manufactured by fermenting inulin using an inulin-degrading enzyme, such as inulin fructotransferase (EC2.4.1.93) produced by Arthrobacter sp.H65-7, or by fermenting levan using levan fructotransferase (EC2.4.1.10) produced by Arthrobacternicotinovorans GS-9, among others. There are five derivatives of DFA, each having a different pattern of two-molecule fructose bond. They are called DFAI, DFAII, DFAIII, DFAIV and DFAV, respectively. DFA mentioned in connection with the present invention applies to all of these DFA derivatives. Among others, however, DFAIII and DFAIV can be favorably used in the present invention because of their high industrial production efficiency and excellent stability after refining.

An oral composition conforming to the present invention contains DFA as an active ingredient and can be utilized as a composition for use in drugs and/or foods and beverages (including feeds for pet animals). For example, it can be used in drugs, foods and beverages, powder milk formulas, enteral nutritional supplements, health foods and drinks, feed additives and any other application that can be orally administered in its final form. The form that can be most favorably used under the present invention is one that delivers DFA and daidzein and/or derivative thereof to the large intestines without being absorbed by the body. One example of such form is an enteric-coated capsule containing an applicable composition. The content of the active ingredient is not specifically limited.

When used as a food or beverage composition, DFA can be used directly or combined with other food or food ingredient in accordance with any commonly used method as deemed necessary. Since DFA has high stability under heat and acid, normal food processing methods can be applied without problem. An oral food composition containing DFA is subject to no limitations in terms of its shape, as it can be used as powder, granule, paste, liquid, suspension, tablet or capsule, among others. For example, such composition can be made into a health drink using various ingredients commonly used in drinks, such as artificial sweeteners, acidifiers and vitamins.

When used as a drug composition, this active ingredient can be administered in various forms.

For example, it can be administered orally as a tablet, capsule, granule, dispersant, or syrup. These formulations can be made according to commonly used methods using the main ingredient with any known auxiliaries commonly found in technologies used to produce medical formulations, such as excipients, binding agents, disintegrating agents, lubricants, flavoring agents, solubilizing agents, suspension agents, and coating agents, among others.

The specific dosage varies depending on the medical condition, age and body weight of the user, as well as the dosage form. When administered orally, the adult dosage should be normally in a range of 0.5 to 2,000 mg, or more preferably in a range of 1 to 1,000 mg, per 1 kg of body weight.

Under the present invention, "daidzein and/or derivative thereof" refers to 4',7-dihydroxy isoflavone and its glycoside and/or acetylated, malonylated or other modified derivative thereof. In particular, daidzein and/or derivative thereof used in the present invention should ideally be a daidzein glycoside or daidzin because it is absorbed slowly by the body and should therefore reach the large intestines in a greater quantity. Under the present invention, daidzein and/or derivative thereof may be derived from a synthetic chemical, plant extract or processed form thereof, or plant itself.

The present invention is explained in greater details using an example below. It should be noted, however, that this is only an example and the present invention is not limited to this example.

Example 1

The ability of DFA to increase equol production in the intestinal tract was examined.

Twenty-seven male Wistar-ST rats (six weeks old) were raised with a solid feed for three days, after which they were divided into three groups by weight so that each group consisted of nine rats. Each group was given a base feed containing 0.25% of a food product containing 40% isoflavone (basal diet group), a feed consisting of the base feed whose sucrose was substituted by 3% with DFAIII (DFAIII group), or a feed consisting of the base feed whose sucrose was substituted by 3% with fructo-oligosaccharide (FOS group), and raised for twenty days. On day 20, blood was taken from each rat through the caudal vein and the equol level in blood plasma was measured using the HPLC-UV method.

The results are shown in Table 1. In the table, a and b indicate that values denoted by different symbols have a significant difference between them.

As evident from these results, ingestion of DFA caused the equol level in blood plasma to rise.

TABLE 1

|  | Equol (umol) |
| --- | --- |
| Basal diet | 11.13 ± 1.22 [a] |
| DFAIII | 17.70 ± 1.81 [b] |
| FOS | 11.23 ± 1.15 [a] |

What is claimed is:

1. A method for increasing a blood equol level in a subject in need thereof, comprising:
    orally administrating to the subject difructose anhydride, and daidzein and/or a derivative thereof in an enteric-coated form in an amount effective to increase equol production by inner-intestinal bacteria in the body,
    wherein fructo-oligosaccharide is not administrated, and
    wherein the daidzein and/or the derivative thereof is selected from the group consisting of 4',7-dihydroxy isoflavone, its glycoside, acetylated, and malonylated derivative thereof.

2. The method according to claim 1, wherein the difructose anhydride is difructose anhydride III or difructose anhydride IV.

3. The method according to claim 1, wherein the administered amount is 0.5 to 2,000 mg of difructose anhydride per 1 kg of body weight.

4. The method according to claim 1, wherein the difructose anhydride is administrated in the form of a food and accounts for 3% of the food.

* * * * *